US00PP16928P2

(12) United States Plant Patent
van den Bosch

(10) Patent No.: US PP16,928 P2
(45) Date of Patent: Aug. 1, 2006

(54) *HYPERICUM* PLANT NAMED 'BOSACLAS'

(50) Latin Name: *Hypericum androsaemum*
Varietal Denomination: Bosaclas

(75) Inventor: Bernard Renee van den Bosch, Rijnsburg (NL)

(73) Assignee: H. & B.R. van den Bosch B.V., Rijnsburg (NL)

( * ) Notice: Subject to any disclaimer, the term of this patent is extended or adjusted under 35 U.S.C. 154(b) by 0 days.

(21) Appl. No.: 11/141,566

(22) Filed: May 31, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

UPOV–ROM Plant Variety Database 2005/05. Search for cultivar Bosaclas.*

* cited by examiner

*Primary Examiner*—Kent Bell
*Assistant Examiner*—Annette H Para
(74) *Attorney, Agent, or Firm*—C. A. Whealy

(57) ABSTRACT

A new and distinct cultivar of *Hypericum* plant named 'Bosaclas', characterized by its upright and outwardly spreading plant habit; medium green-colored leaves; freely flowering habit; glossy red-colored fruits; and good post-production longevity.

2 Drawing Sheets

Botanical designation: *Hypericum androsaemum.*
Cultivar denomination: 'Bosaclas'.

BACKGROUND OF THE INVENTION

The present Invention relates to a new and distinct cultivar of *Hypericum* plant, botanically known as *Hypericum androsaemum,* commercially used as cut stems with fruits, and hereinafter referred to by the name 'Bosaclas'.

The new *Hypericum* is a product of a planned breeding program conducted by the Inventor in Rijnsburg, The Netherlands. The objective of the breeding program was to develop cut *Hypericum* varieties with attractive fruit coloration.

The new cultivar originated from a cross-pollination made by the Inventor in 1996 of a proprietary selection of *Hypericum androsaemum* identified as code number 93, not patented, as the female, or seed, parent with a proprietary selection of *Hypericum androsaemum* identified as code number 71, not patented, as the male, or pollen, parent. The cultivar Bosaclas was discovered and selected by the Inventor in 1998 as a flowering plant within the progeny of the stated cross-pollination in a controlled environment in Rijnsburg, The Netherlands.

Asexual reproduction of the new *Hypericum* by terminal cuttings taken at Rijnsburg, The Netherlands since 1999, has shown that the unique features of this new *Hypericum* are stable and reproduced true to type in successive generations of asexual reproduction.

SUMMARY OF THE INVENTION

The following traits have been repeatedly observed and are determined to be the unique characteristics of 'Bosaclas'. These characteristics in combination distinguish 'Bosaclas' as a new and distinct cultivar:

1. Upright and outwardly spreading plant habit.
2. Medium green-colored leaves.
3. Freely flowering habit.

4. Glossy red-colored fruits.
5. Good postproduction longevity.

Plants of the new *Hypericum* differ from plants of the parent selections primarily in fruit coloration.

Plants of the new *Hypericum* can be compared to plants of the *Hypericum* cultivar Bosapin, disclosed in U.S. Plant Pat. No. 10,993. In side-by-side comparisons conducted in Rijnsburg, The Netherlands, plants of the new *Hypericum* differed from plants of the cultivar Bosapin in the following characteristics:

1. Plants of the new *Hypericum* had smaller leaves than plants of the cultivar Bosapin.
2. Plants of the new *Hypericum* had lighter green-colored leaves than plants of the cultivar Bosapin.
3. Plants of the new *Hypericum* had larger fruits than plants of the cultivar Bosapin.
4. Plants of the new *Hypericum* had darker red-colored fruits than plants of the cultivar Bosapin.

BRIEF DESCRIPTION OF THE PHOTOGRAPHS

The accompanying colored photographs illustrate the overall appearance of the new *Hypericum,* showing the colors as true as it is reasonably possible to obtain in colored reproductions of this type. Colors in the photographs may differ slightly from the color values cited in the detailed botanical description which accurately describe the colors of the new *Hypericum.*

The photograph at the top of the first sheet comprises a side perspective view of typical plants of 'Bosaclas' with flowers and fruits grown in a ground bed.

The photograph at the bottom of the first sheet is a close-up view of the upper surface of a typical leaf of 'Bosaclas'.

The photograph at the top of the second sheet is a close-up view of typical flowers and fruits of 'Bosaclas'.

The photograph at the bottom of the second sheet is a close-up view of typical fruits of 'Bosaclas'.

DETAILED BOTANICAL DESCRIPTION

The new *Hypericum* has not been observed under all possible environmental conditions. The phenotype may vary somewhat with variations in environment such as temperature, daylength and light intensity, without, however, any variance in genotype.

The aforementioned photographs, following observations and measurements describe plants grown in Rijnsburg, The Netherlands, in an outdoor nursery and under commercial production practices. Plants were about two years old. The photographs and description were taken in August, 2004, when outdoor day temperatures ranged from 17 to 33° C. and night temperatures ranged from 7 to 19° C. In the following description, color references are made to The Royal Horticultural Society Colour Chart, 2001 Edition, except where general terms of ordinary dictionary significance are used.

Botanical classification: *Hypericum androsaemum* cultivar Bosaclas.

Parentage:

*Female parent.*—Proprietary selection of *Hypericum androsaemum* identified as code number 93, not patented.

*Male parent.*—Proprietary selection of *Hypericum androsaemum* identified as code number 71, not patented.

Propagation:

*Type.*—Terminal cuttings.

*Time to initiate roots.*—Summer: About 14 days at 20° C. Winter: About 21 days at 15° C.

*Time to produce a rooted cutting.*—Summer: About two months at 20° C. Winter: About three months at 15° C.

*Root description.*—Fine; white in color.

*Rooting habit.*—Freely branching, dense.

Plant description:

*Plant form.*—Upright and outwardly spreading perennial woody shrub; broad inverted triangle.

*Growth habit.*—Moderately vigorous. Freely basal branching; dense and bushy growth habit.

*Plant height.*—About 68 cm.

*Plant width (spread).*—About 78 cm.

*Quantity of stems per year.*—About twelve; production of stems increases with age of plants.

*Lateral branches.*—Length: About 17.9 cm. Diameter: About 3 mm. Internode length: About 4.2 to 8.2 cm. Strength: Moderately strong. Texture: Smooth; glabrous. Color: 145A overlain with 183B; with development, N199D to 200A.

*Foliage description.*—Arrangement: Opposite, simple; sessile. Length: About 6.8 cm. Width: About 4.2 cm. Shape: Ovate. Apex: Obtuse. Base: Obtuse to slightly cordate. Margin: Entire. Texture, upper and lower surfaces: Glabrous; slightly rugose. Venation pattern: Pinnate. Color: Developing leaves, upper surface: 146A to 146B. Developing leaves, lower surface: 146B to 146C. Fully expanded leaves, upper surface: 137A. Fully expanded leaves, lower surface: 138B. Venation, upper and lower surfaces: 144B to 144C.

Flower description:

*Flower type and habit.*—Bright yellow single flowers arranged in terminal compound umbels with about ten flowers per lateral branch. Flowers not fragrant. Flowers not persistent. Flowers face upright.

*Natural flowering season.*—Summer, typically July through August in The Netherlands; flowering period typically lasts about 45 days.

*Postproduction longevity.*—Cut stems are typically harvested when all flowers have developed fruits. Postproduction longevity of cut stems with fruits more than one week.

*Inflorescence height.*—About 5.6 cm.

*Inflorescence diameter.*—About 8.8 cm.

*Flower buds.*—Height: About 1 cm. Diameter: About 7 mm. Shape: Obovate. Color: 12A; towards the apex, 26A.

*Flowers.*—Diameter: About 3.8 cm. Depth: About 1.9 cm.

*Petals.*—Quantity per flower: Typically five. Length: About 1.6 cm. Width: About 1.1 cm. Shape: Obovate. Aspect: Slightly concave. Apex: Obtuse. Base: Attenuate. Margin: Entire. Texture, upper and lower surfaces: Smooth, glabrous. Color: Developing and fully expanded petals, upper surface: 12A to 13A; color becoming closer to 10A with development. Developing and fully expanded petals, lower surface: 11A; towards the apex, 13B.

*Sepals.*—Quantity per flower: Typically five. Length: About 8 mm. Width: About 6 mm. Shape: Broadly ovate. Apex: Obtuse. Base: Broadly cuneate. Margin: Entire. Aspect: Flat. Texture, upper and lower surfaces: Smooth, glabrous. Color: Developing sepals, upper and lower surfaces: 144A; towards the base, 183C. Fully developed sepals, upper surface: 143A to 144A; towards the base, 183C. Fully developed sepals, lower surface: 144B; towards the base, 183C to 183D.

*Peduncles.*—Length: About 4 cm. Diameter: About 2 mm. Orientation: Mostly erect. Strength: Moderately strong. Color: 145A overlain with 183B.

*Pedicels.*—Length: About 1.3 cm. Diameter: About 1.5 mm. Orientation: Erect to about 55° from vertical. Strength: Moderately strong. Color: 146A overlain with 183B.

*Reproductive organs.*—Stamens: Quantity per flower: About 85. Anther shape: Broadly oval. Anther length: About 0.5 mm. Anther color: 15A. Filament length: About 1.9 cm. Filament color: 12A; towards the base, 13A. Pollen amount: Scarce. Pollen color: 12A to 12B. Pistils: Quantity per flower: Typically three. Pistil length: About 8.5 mm. Stigma shape: Globular. Stigma color: Close to 183C to 183D. Style length: About 8 mm. Style color: 1B. Ovary color: 1B.

*Fruits.*—Quantity per flower: One. Days to ripening: About 25. Longevity on the plant: About 30 days. Type: Capsule. Shape: Ellipsoidal. Length: About 1.7 cm. Diameter: About 1.3 cm. Texture: Smooth, glabrous. Luster: Glossy. Color: 45A to 45B.

*Seeds.*—Quantity per fruit: Typically more than 100. Length: About 0.8 mm. Diameter: About 0.5 mm. Texture: Smooth, glabrous. Color: 199A to N199A.

Disease/pest resistance: Plants of the new *Hypericum* have not been observed to be resistant to pathogens and pests common to *Hypericum*.

Temperature tolerance: Plants of the new *Hypericum* have been observed to tolerate temperatures ranging from −15 to 35° C.

It is claimed:

1. A new and distinct cultivar of *Hypericum* plant named 'Bosaclas', as illustrated and described.

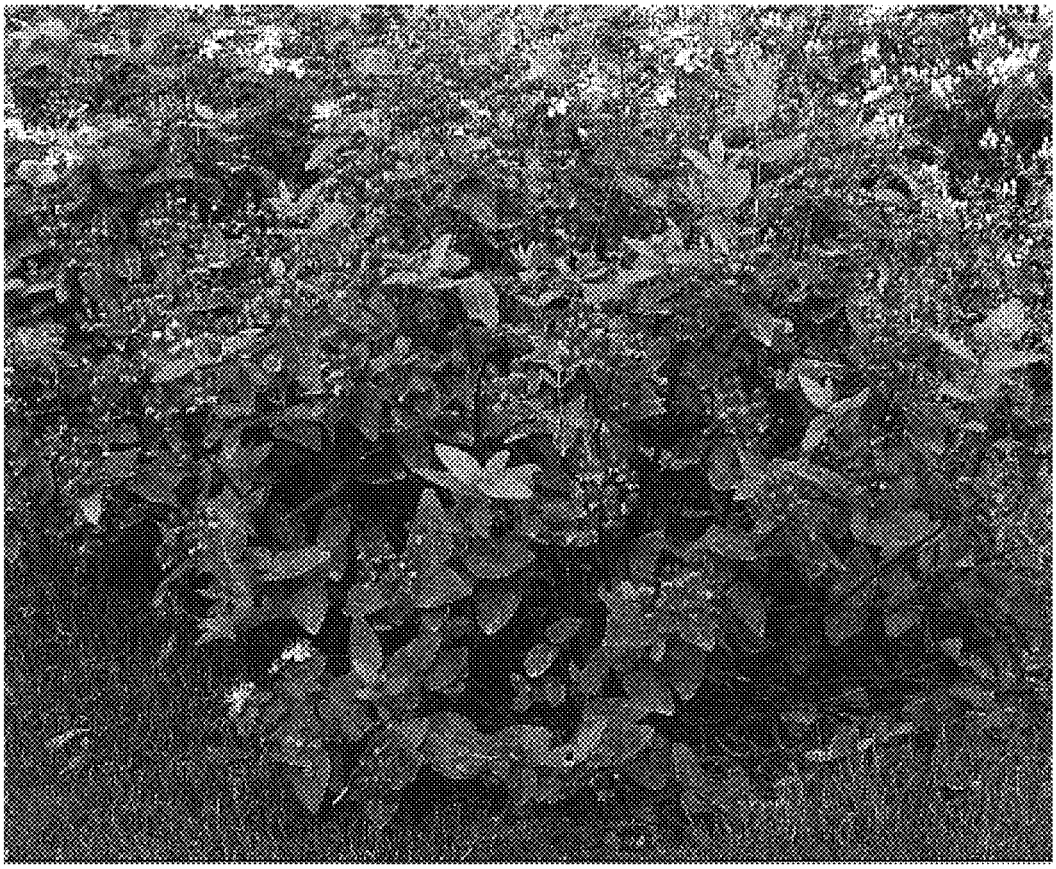
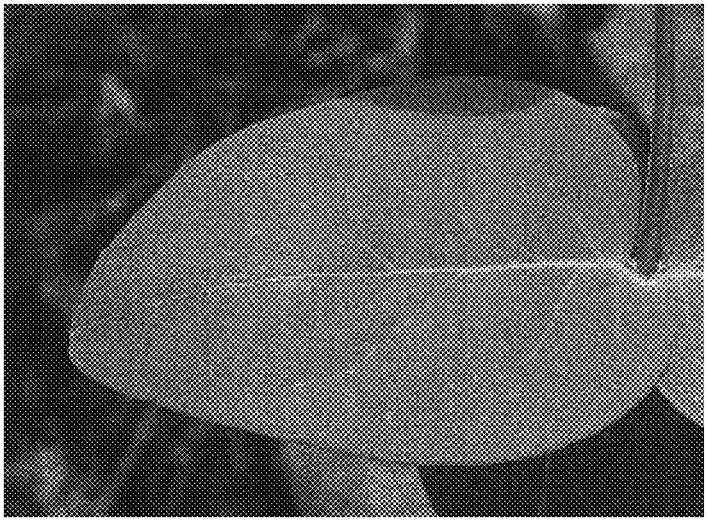

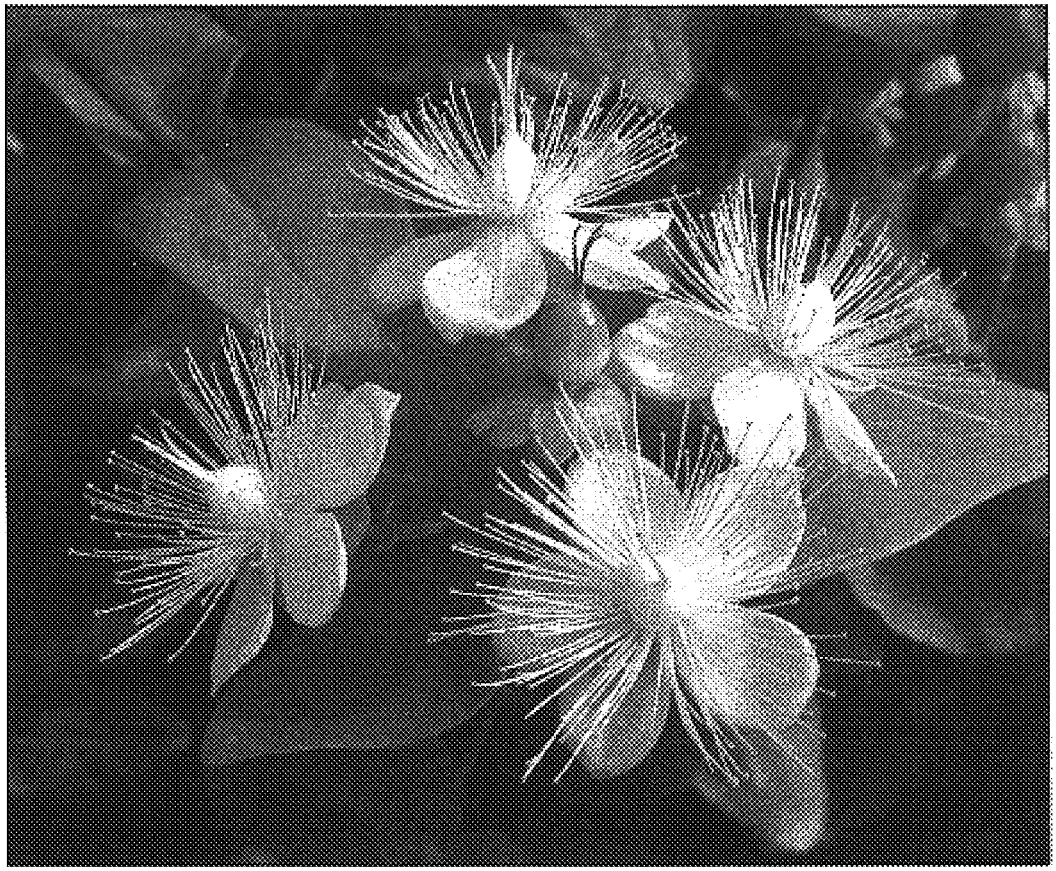
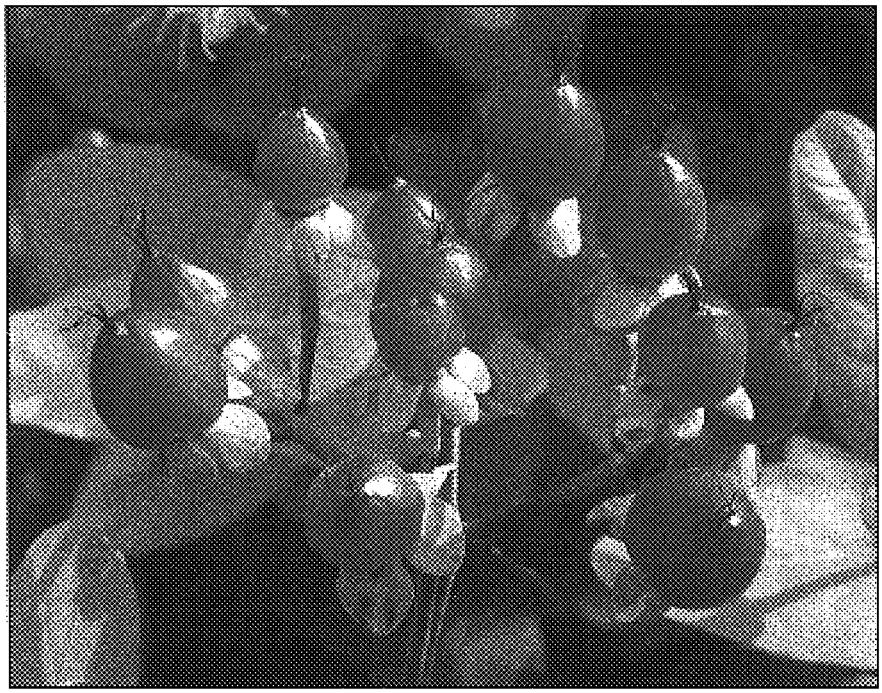

* * * * *